(12) United States Patent
Yeh et al.

(10) Patent No.: US 6,844,479 B2
(45) Date of Patent: Jan. 18, 2005

(54) ALKYLATION PROCESS

(75) Inventors: Chuen Y. Yeh, Edison, NJ (US); Xingtao Gao, Edison, NJ (US); Philip J. Angevine, Woodbury, NJ (US)

(73) Assignee: ABB Lummus Global Inc., Bloomfield, NJ (US)

(*) Notice: Subject to any disclaimer, the term of this patent is extended or adjusted under 35 U.S.C. 154(b) by 103 days.

(21) Appl. No.: 10/422,464

(22) Filed: Apr. 24, 2003

(65) Prior Publication Data

US 2004/0010176 A1 Jan. 15, 2004

Related U.S. Application Data

(63) Continuation-in-part of application No. 09/981,926, filed on Oct. 17, 2001.
(60) Provisional application No. 60/242,110, filed on Oct. 20, 2000.

(51) Int. Cl.$^7$ .............................. C07C 6/00; C07C 2/54
(52) U.S. Cl. ...................... 585/643; 585/646; 585/709; 585/710; 585/713
(58) Field of Search ................................ 585/643, 646, 585/709, 710, 713, 446, 470

(56) References Cited

U.S. PATENT DOCUMENTS

| | | | |
|---|---|---|---|
| 3,308,069 A | 3/1967 | Wadlinger et al. | 502/62 |
| 4,746,763 A * | 5/1988 | Kocal | 585/417 |
| 5,116,794 A | 5/1992 | Skeels et al. | 502/85 |
| 5,139,759 A | 8/1992 | Cannan et al. | 423/709 |
| 5,164,169 A | 11/1992 | Rubin | 423/709 |
| 5,164,170 A | 11/1992 | Rubin | 423/709 |
| 5,256,392 A | 10/1993 | Shamshoum | 423/717 |
| 5,258,570 A | 11/1993 | Skeels et al. | 585/739 |
| 5,427,765 A | 6/1995 | Inoue et al. | 423/705 |
| 5,457,078 A | 10/1995 | Absil et al. | 502/62 |
| 5,895,828 A * | 4/1999 | Yao et al. | 585/418 |
| 5,980,859 A | 11/1999 | Gajda et al. | 423/713 |
| 5,986,158 A | 11/1999 | Van Broekhoven et al. | 585/475 |
| 6,004,527 A | 12/1999 | Murrell et al. | 423/712 |
| 6,303,530 B1 * | 10/2001 | Schwartz et al. | 502/66 |
| 2002/0111522 A1 | 8/2002 | Overbeek et al. | |

* cited by examiner

Primary Examiner—Walter D. Griffin
Assistant Examiner—Tam M. Nguyen
(74) Attorney, Agent, or Firm—Dilworth & Barrese, LLP

(57) ABSTRACT

A process for the alkylation of paraffins with olefins includes contacting the paraffin with the olefin under alkylation conditions with a zeolite having an AAI number of at least about 1.0. In a preferred process isobutane is alkylated with cis-2-butene to produce a high octane (RON) gasoline product containing trimethylpentane isomers.

15 Claims, 1 Drawing Sheet

ALKYLATION PROCESS

CROSS-REFERENCE TO RELATED APPLICATION(S)

The present application is a continuation-in-part of U.S. application Ser. No. 09/981,926, filed Oct. 17, 2001, which claims priority to provisional application Ser. No. 60/242,110 filed Oct. 20, 2000 to which priority is claimed herein.

BACKGROUND

1. Technical Field

The present disclosure relates to a process for the alkylation, and particularly to a process for the alkylation of paraffins with olefins to produce gasoline products.

2. Background of the Art

Alkylation processes for the manufacture of high octane gasoline products are known. Typically, such processes are directed to the alkylation of paraffins with olefins to produced branched hydrocarbon molecules for gasoline components such as isomers of trimethylpentane (TMP), which have high octane numbers. High octane number, i.e., research octane number ("RON"), is important for gasoline, especially gasolines for use in high performance automobile engines to prevent engine knock.

Liquid alkylation using acid catalysts is a commonly used method for olefin-paraffin alkylation. Two commonly used processes employ sulfuric acid or hydrofluoric acid. However, both of these methods suffer from severe environmental hazards. Both acids are highly corrosive and dangerous if released.

Solid olefin-paraffin alkylation processes are also known. Such processes typically employ a solid catalyst such as transition metals or metals of Group VIII of the Periodic Table of the Elements (particularly noble metals) in combination with a zeolite, silica, alumina, silica-alumina, oxides of transition metals such as zirconium, molybdenum, tungsten, titanium or tin, for example.

Suitable zeolites for use as solid olefin-paraffin alkylation include zeolite Y, HY, USY, zeolite beta, MCM-22 and MCM-36, for example.

U.S. Pat. No. 5,986,158, which is herein incorporated by reference, discloses a process for alkylating hydrocarbons in which an alkylatable organic compound is reacted with an alkylating agent to form an alkylate in the presence of a catalyst providing a hydrogenating function and a solid acid constituent, with the catalyst being subjected intermittently to a regeneration step by being contacted with a feed containing a saturated hydrocarbon and hydrogen.

A problem remains with solid catalyst alkylation processes in that the catalyst has a relatively short on-stream life and needs to be repeatedly regenerated. Clearly, it would be desirable to have a catalyst with a longer on-stream life, thereby requiring less frequent regeneration cycles.

SUMMARY OF THE INVENTION

A process for the alkylation of paraffins with olefins which comprises contacting the paraffin with the olefin under alkylation conditions with a zeolite having an AAI (acidity-activity index) number of at least about 1.0.

BRIEF DESCRIPTION OF THE DRAWINGS

Various embodiments are described herein with reference to the drawings wherein.

DETAILED DESCRIPTION OF PREFERRED EMBODIMENT(S)

Figure 1:
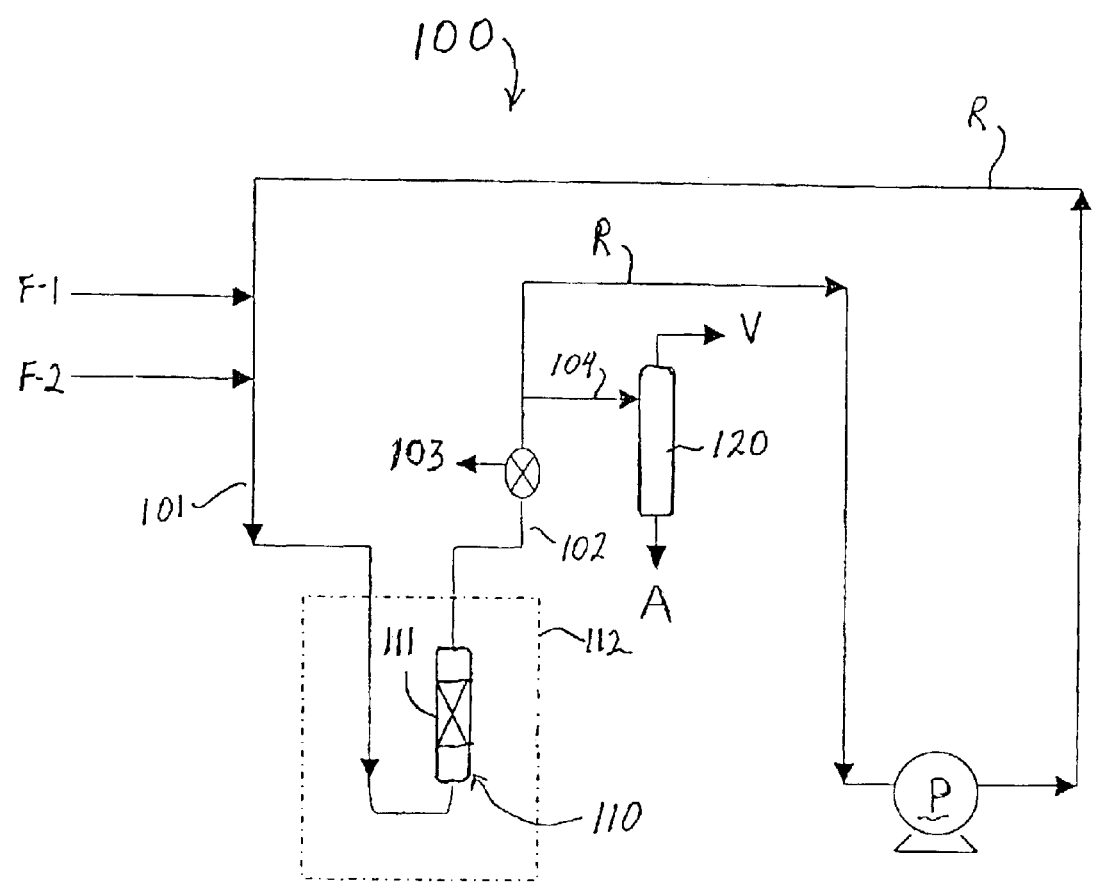
FIG. 1 is a diagrammatic illustration of an alkylation system in which the catalyst of the present invention can be used.

The present invention employs a zeolite as a catalyst for the alkylation of a paraffin with an olefin to produce a gasoline product. The zeolite is prepared in accordance with the method described in U.S. patent application Ser. No. 09/981,926.

U.S. patent application Ser. No. 09/981,926, filed Oct. 17, 2001, which is herein incorporated by reference, teaches that the performance of a zeolite is significantly affected by changing the state or characteristics of the zeolite. Controlled heat treatment or calcining to remove the organic templating agent in the zeolite creates acid sites of a specific nature and strength, and an average pore structure of a specific volume and size.

The current working model is that the so-called "strong acid sites" are reduced primarily as a result of a loss of a specific type of tetrahedral aluminum. As a result, in accordance with an aspect of the present invention, in producing a zeolites or molecular sieve, processing conditions that reduce the amount of the specific type of tetrahedral aluminum and thereby reduce the number of strong acid sites should be minimized or avoided in order to provide for improved catalyst activity. In order to minimize the loss of the specific tetrahedral aluminum and thereby maintain a certain minimum amount of strong acid sites, the conditions at which the templating agent is removed should be controlled so as to reduce and/or eliminate exposure to temperatures above about 550° C. for a prolonged period of time. In addition, in a preferred embodiment steaming should be avoided, for example, by slow heating to the final calcination temperature.

Moreover, processing of the zeolites or molecular sieve after the removal of the templating agent should also be controlled to reduce and/or eliminate exposure to temperatures above about 550° C. For example, the exchange steps and final calcination of the ion exchanged zeolite or molecular sieve should occur at moderate temperatures. Ion exchange includes, but is not limited to, exchange of Na with $NH_4NO_3$ to produce the $NH_4$-form of the zeolite or molecular sieve. In addition, use of organic agents (e.g., to increase strength, to facilitate extrudability, etc.) in procedures for extruding the zeolites or molecular sieve into a desired shape or form should also be minimized or avoided.

The prior art did not recognize that strong acid sites in zeolites and molecular sieves increase catalytic activity and that processing conditions for producing zeolites and molecular sieves should be controlled to prevent loss of strong acid sites. In the prior art, processing steps after formation of the zeolites or molecular sieve reduced the number of strong acid sites to values below those of the present invention, and such reduction resulted in a reduction in catalytic activity.

More particularly, in a preferred embodiment the zeolite or molecular sieve is one that contains silica and alumina in a silica to alumina molar ratio of 6:1 or higher or 15:1 or higher that is prepared by use of a templating or organic directing agent that includes an organic nitrogen compound. As representative but non-limiting examples of zeolites there may be mentioned: zeolite beta, zeolite L, TEA-mordenite, MCM-22, MCM-36, MCM-39, MCM-41, MCM-48, PSH-3, ZSM-5, Breck-6 (also known as EMT), ZSM-11, ZSM-12, ZSM-22, ZSM-23, ZSM-35, ZSM-48, SSZ-32, TUD-1, etc. A preferred zeolite is zeolite beta although the invention is not limited to the preferred zeolite. Zeolite beta is commercially available, and methods for preparing or modifying zeolite beta are disclosed, for example, in U.S. Pat. Nos. 3,308,069, 5,116,794, 5,139,759, 5,164,169, 5,164,170, 5,256,392, 5,258,570, 5,427,765, 5,457,078, 5,980,859 and 6,004,527.

The zeolites and molecular sieves of the present invention may be combined with other materials, as known in the art. For example, zeolites and molecular sieves may optionally be metal cation exchanged following the hydrogen forming cation exchange. If the zeolites and molecular sieves are metal cation exchanged after the hydrogen forming cation exchange, the zeolites or molecular sieve component thereof preferably includes a number of acid sites as hereinabove described. For alkylation, particularly suitable metal cations include Group VIII noble metals, such as platinum, palladium, iridium and the like. The use of such metal cations is known in the art and the incorporation of such additional metal cations, and the amount thereof is deemed to be within the skill of the art from the teachings herein. Similarly, the zeolites or molecular sieve may be employed with one or more inorganic oxide matrix components, which is generally combined with zeolites and molecular sieves during the exchange with a metal cation if used. Such matrix components are general inorganic oxides such as silica-aluminas, clays, aluminas, silicas, etc. The matrix may be in the form of a sol, hydrogel or gel and is generally an alumina, silica or silica-alumina component such as a conventional silica-alumina catalyst. The matrix may be catalytically active or inert. In a preferred embodiment, when combined with a matrix, the zeolite component has a number of strong acid sites, as herein described.

In accordance with a further aspect of the present invention, zeolites having an improved catalytic activity may be produced by increasing the strong acid sites thereof. In this respect, during the procedures for producing zeolites, and in particular the procedure for removing the organic nitrogen templating agent, the conditions employed therein should be controlled to preserve strong acid sites. In this respect, strong acid sites are maintained by employing process conditions which prevent loss of those sites that are proven to be beneficial in catalytic conversion applications. While not wishing to be bound to any particular theory, it is believed that those sites can be ascribed to be a specific kind of tetrahedral aluminum sites in the zeolite structure.

In this respect, in removing the organic nitrogen templating agent (in general, at least 50% thereof is removed and in a preferred embodiment substantially all is removed), heating is controlled to prevent exposure to average temperatures that are above about 575° C. and preferably the heating is to an average temperature of no greater than 550° C., preferably no more than about 500° C.

Moreover, in a preferred embodiment, heating should be carefully controlled to avoid local overheating to temperatures above about 575° C. Preferably, during calcining the temperature is raised gradually, for example, at a rate of no more than about 10° C./min, more preferably no more than about 5° C./min to an intermediate temperature (e.g., about 120° C. or other suitable temperature), held for a period of time at that temperature, and then gradually raised again to the calcining temperature.

Applicant has surprisingly found that controlled heat treatment or calcination to remove the organic directing agent and exposure of the zeolite or molecular sieve during this treatment to average temperatures no higher than 550° C. is desired to create acid sites of a specific nature and strength. These created acid sites, as can be measured by the temperature programmed desorption of ammonia ("ammonia TPD") performed in accordance with Example 3 of U.S. patent application Ser. No. 09/981,926, are surprisingly found to significantly enhance catalytic performance in reactions, such as, but not limited to, hydrocarbon conversion technologies. Applicant has found that, contrary to what has been recognized by prior art findings, that the abundance of these sites, referred to as "strong acid sites" and measured by ammonia TPD, is beneficial in alkylation technologies. Applicant has also found, that in addition to the appearance of such acid sites, substantial restructuring of the zeolite or molecular sieve occurs, as can be characterized using porosity measurements, such as $N_2$ physisorption and/or mercury porosimetry. According to the current understanding, Applicant believes that a combination of the above-mentioned characteristics of zeolites and molecular sieves is desirable in optimizing performance in catalytic applications, specifically in hydrocarbon conversion applications. The combination of the above-mentioned improved characteristic and enhanced catalytic performance is found to be characterized by the Acidity-Activity Index ("AAI"). The AAI, as used herein in the Specification and claims, is the ratio of the total ammonia desorbed from the zeolite at a temperature above 300° C. to the total ammonia desorbed from the zeolite at a temperature below 300° C. as can be measured by the temperature controlled desorption (TPD) performed in accordance with Example 3 of U.S. application Ser. No. 09/981,926. In accordance with a preferred embodiment of the present invention, the zeolite of the invention has an Acidity-Activity Index (AAI) of at least 1.0, preferably at least 1.2, and more preferably at least 1.4, and most preferably at least 1.6.

The catalyst used in the process herein includes a hydrogenation function provided by a Group VIII noble metal component, preferably platinum, palladium, or combinations thereof. The catalyst generally contains from about 0.01 wt % to about 2.0 wt % of the noble metal, preferably 0.1 wt % to about 1.0 wt % of the noble metal component The production of the high octane gasoline component TMP isomers is generally accomplished by alkylating isobutane with cis-2-butene. While the present application is particularly advantageous for the production of TMP isomers, it should be recognized that any other alkylatable paraffins and olefins can alternatively be employed, for example, $C_4$–$C_6$ isoparaffins and $C_2$–$C_6$ olefins.

Alkylation conditions typically include a temperature of from about 40° C. to about 120° C., preferably from about 60° C. to about 90° C., a pressure of from about 100 psig to about 500 psig, preferably from about 250 psig to about 350 psig, and a WHSV (grams alkylating agent per grams catalyst per hour) of from about 0.05 to about 1.0, preferably from about 0.1 to about 0.5.

Referring now to FIG. 1, a system 100 for the alkylation of a paraffin with an olefin as used for the Examples given below is illustrated. System 100 employs a recycle stream R to which the feed streams F-1 (olefin) and F-2 (iso-paraffin) are joined. In a preferred embodiment the olefin stream F-1 comprises cis-2-butene and the iso-paraffin stream comprises isobutane. The combined streams are sent via line 101 to alkylation reactor 110 which contains a fixed bed 111 of the catalyst of the invention. The alkylation reactor is immersed in an oil bath 112 to maintain the predetermined reaction temperature. A sample can be drawn off at port 103 from the effluent stream 102 of the alkylation reactor 110. The effluent is divided into a recycle stream R, which is circulated by pump P back to the alkylation reactor 110 after the addition of fresh feed F-1 and F-2, and stream 104 which is sent to a separation drum 120, from which vapor V is drawn off from the top and product alkylate A (e.g., TMP isomers) is withdrawn from the bottom.

The following Examples illustrate features of the present invention. In the Examples the reactor system 100 illustrated in FIG. 1 was employed. Reactor 110 was a differential fixed-bed reactor to maintain a high isobutane to butene ratio and simulate a continuous stirred tank reactor (CSTR). High isobutane/butene ratios help to minimize the formation of coke and high boiling compounds which deactivate the catalyst. A fixed bed reactor can be used with several butene injection points at different bed height locations to maintain the desired isobutane/butene ratio at any given location and overall across the catalyst bed. The reaction product was a mixture of various components and/or isomers. The preferred alkylation components are isomers of TMP branched $C_8$ hydrocarbons, which have high research octane numbers (RON). For example, 2,2,4-trimethylpentane (isooctane) has a RON value of 100. The total RON value of the product alkylate of the Examples was obtained by summation of the product of the weight fraction of each component (obtained from gas chromatographic (GC) analysis) multiplied by the octane number of the component. The experiments were continued until a drop in TMP production was observed. The catalyst longevity is determined by the time olefin breakthrough occurred due to aging. At this point, olefin peaks on the gas chromatograph analysis indicated deactivation of the catalyst.

EXAMPLE 1

The catalyst used in this Example included zeolite beta produced in accordance with the method set forth in U.S. patent application Ser. No. 09/981,926 and had an estimated AAI value of 1.2. The zeolite was combined with alumina to form a catalyst of 1/16" extrudates containing 80 wt % zeolite. The catalyst was then sieved to a particle size of −18 to +25 mesh and ion exchanged at room temperature with tetraamine platinum (II) hydroxide hydrate (59% Pt) to produce a catalyst containing 0.5 wt % Pt on zeolite. The catalyst was pretreated by heating from room temperature to 350° C. at a rate of 0.5° C./min in flowing air (75 ml/min/gram), holding under those conditions for 2 hours, then cooling down to room temperature, then switching to hydrogen flow of 20 ml/min/gram while heating to 275° C. at the rate of 1° C./min, holding for 2 hours and then allowing the catalyst to cool to room temperature. The total catalyst charge to the reactor (i.e., zeolite plus binder, Pt exchanged and pretreated.) was 4.0 parts, and 0.27 parts/min of a feed containing isobutane and cis-2-butene at an isobutane/cis-2-butene ratio of 15.9 was pumped in from the start of the test run. Samples were taken from sample port 103 with a high pressure syringe every 45 minutes for GC analysis until a drop in TMP isomers was observed.

The results of the alkylation test are set forth in Table 1 below.

EXAMPLE 2

The catalyst used in this Example also included zeolite beta produced in accordance with the method set forth in U.S. patent application Ser. No. 09/981,926 and had an estimated AAI value of 1.2. The zeolite was combined with alumina to form a catalyst of 1/16" extrudates containing 80 wt % zeolite. The catalyst pretreatment conditions and the alkylation reaction equipment set-up and conditions were the same as in Example 1. The total catalyst charge to the reactor (i.e., zeolite plus binder, Pt exchanged and pretreated.) was 4.0 parts, and 0.27 parts/min of a feed containing isobutane and cis-2-butene at an isobutane/cis-2-butene ratio of 15.9 was pumped in from the start of the test run. Samples were taken from sample port 103 with a high pressure syringe every 45 minutes for GC analysis until a drop in TMP isomers was observed. The results of the alkylation test are set forth below in Table 1.

The Comparative Examples set forth below employ conventional catalysts and are not in accordance with the invention.

Comparative Example A

The catalyst used in this Example included conventional zeolite beta obtained from Zeolyst International Co. of Valley Forge, Pa., and had an estimated AAI number of about 0.95. The zeolite was combined with alumina to form a catalyst of 1/16" extrudates containing 80 wt % zeolite. The catalyst was then sieved to a particle size of −18 to +25 mesh and ion exchanged at room temperature with tetraamine platinum (II) hydroxide hydrate (59% Pt) to produce a catalyst containing 0.5 wt % Pt on zeolite. The catalyst pretreatment conditions and the alkylation reaction equipment set-up and conditions were the same as in Examples 1 and 2. The total catalyst charge to the reactor (i.e., zeolite plus binder, Pt exchanged and pretreated) was 4.0 parts, and 0.27 parts/min of a feed containing isobutane and cis-2-butene at an isobutane/cis-2-butene ratio of 15.9 was pumped in from the start of the test run. Samples were taken from sample port 103 with a high pressure syringe every 45 minutes for GC analysis until a drop in TMP isomers was observed. The results of the alkylation test are set forth below in Table 1.

Comparative Example B

The catalyst used in this Example included conventional zeolite Y obtained from Akzo-Nobel Co. The zeolite was combined with alumina to form a catalyst of 1/16" extrudates containing 70 wt % zeolite. The catalyst was then sieved to a particle size of −18 to +25 mesh and ion exchanged at room temperature with tetraamine platinum (II) hydroxide hydrate (59% Pt) to produce a catalyst containing 0.5 wt % Pt on zeolite. The catalyst pretreatment conditions and the alkylation reaction equipment set-up and conditions were the same as in Examples 1 and 2. The total catalyst charge to the reactor (i.e., zeolite plus binder, Pt exchanged and pretreated) was 4.0 parts, and 0.27 parts/min of a feed containing isobutane and cis-2-butene at an isobutane/cis-2-butene ratio of 15.9 was pumped in from the start of the test run. Samples were taken from sample port 103 with a high pressure syringe every 45 minutes for GC analysis until a drop in TMP isomers was observed. The results of the test are set forth below in Table 1.

TABLE 1

| Example or Comparative Example | Catalyst | Olefin Breakthrough (hrs) | TMP drop (hrs) | RON |
|---|---|---|---|---|
| Example 1 | Zeolite beta (invention) | 3.5 | 4.5 | 96.0 |
| Example 2 | Zeolite beta (invention) | 3.8 | 4.5 | 96.0 |
| Comparative Example A | Zeolite beta (commercial) | 1.1 | 2.3 | 95.7 |
| Comparative Example B | Zeolite Y (commercial) | 1.2 | 4.5 | 96.4 |

As can be seen from the above results, the catalyst of the present invention provided about three times longer on-stream time before olefin breakthrough as compared with conventional zeolite beta and zeolite Y, while still providing a gasoline product having a comparably high octane number.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A process for the alkylation of paraffins with olefins which comprises:

contacting the paraffin with the olefin under alkylation conditions with a zeolite having an AAI number of at least about 1.0.

2. The process of claim 1 wherein the paraffin is isobutane and the olefin is cis-2-butene and a product of the alkylation process includes trimethylpentane isomers.

3. The process of claim 1 wherein the zeolite is selected from the group consisting of zeolite beta, zeolite L, TEA-mordenite, MCM-22, MCM-36, MCM-39, MCM-41, MCM-48, PSH-3, ZSM-5, Breck-6, ZSM-11, ZSM-12, ZSM-22, ZSM-23, ZSM-35, ZSM-48, SSZ-32 and TUD-1.

4. The process of claim 1 wherein the zeolite is zeolite beta.

5. The process of claim 1 wherein the zeolite has an AAI number of at least about 1.2.

6. The process of claim 1 wherein the zeolite has an AAI number of at least about 1.4.

7. The process of claim 1 wherein the zeolite has an AAI number of at least about 1.6.

8. The process of claim 1 wherein the alkylation reaction conditions include a temperature of from about 40° C. to about 120° C., a pressure of from about 100 psig to about 500 psig, and a WHSV of from about 0.05 to about 1.0.

9. The process of claim 1 wherein the alkylation reaction conditions include a temperature of from about 60° C. to about 90° C., a pressure of from about 250 psig to about 350 psig, and a WHSV of from 0.1 to about 0.5.

10. The process of claim 1 wherein the zeolite contains from about 0.01 wt % to about 2.0 wt % of a noble metal.

11. The process of claim 10 wherein the noble metal is selected from the group consisting of platinum, palladium and combinations thereof.

12. The process of claim 1 wherein the zeolite is combined with a binder.

13. The process of claim 12 wherein the binder is alumina.

14. The process of claim 1 wherein the zeolite is pretreated by calcination to remove organic templating agent at a temperature of no more than about 550° C.

15. The process of claim 1 wherein the zeolite is pretreated by calcination to remove organic templating agent at a temperature of no more than about 500° C.

* * * * *